US00PP16439P2

(12) United States Plant Patent
Brown

(10) Patent No.: US PP16,439 P2
(45) Date of Patent: Apr. 11, 2006

(54) ***PETUNIA* PLANT NAMED 'MP209'**

(50) Latin Name: *Petunia×hybrida*
Varietal Denomination: MP209

(75) Inventor: Graham Noel Brown, Pennant Hills (AU)

(73) Assignee: Nuflora International Pty. Ltd., Macquarie Fields (AU)

( * ) Notice: Subject to any disclaimer, the term of this patent is extended or adjusted under 35 U.S.C. 154(b) by 49 days.

(21) Appl. No.: 11/091,846

(22) Filed: Mar. 28, 2005

(51) Int. Cl.
*A01H 5/00* (2006.01)

(52) U.S. Cl. ..... Plt./356
(58) Field of Classification Search ..... Plt./356
See application file for complete search history.

(56) References Cited

U.S. PATENT DOCUMENTS

PP12,139 P2 * 10/2001 Rother ..... Plt./356
PP14,998 P2 * 7/2004 Brown ..... Plt./356
PP15,786 P2 * 6/2005 Hanes ..... Plt./356

OTHER PUBLICATIONS

UPOV ROM GTITM Computer Database, GTI Jouve Retrieval Software 2005/02 Citation for 'MP209'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Petunia* plant named 'MP209', characterized by its compact, low mounding and outwardly spreading plant habit; freely branching and vigorous growth habit; numerous small bright pink to light red purple-colored flowers; and good garden performance.

1 Drawing Sheet

Botanical designation: *Petunia×hybrida.*
Cultivar denomination: 'MP209'.

BACKGROUND OF THE INVENTION

The present Invention relates to a new and distinct cultivar of *Petunia* plant, botanically known as *Petunia×hybrida*, and hereinafter referred to by the cultivar name MP209.

The new *Petunia* is a product of a planned breeding program conducted by the Inventor in Cobbitty, New South Wales, Australia. The objective of the breeding program is to create outwardly spreading *Petunias* with numerous small flowers with attractive flower colors.

The new *Petunia* originated from a cross-pollination made by the Inventor in December, 2001 of a proprietary *Petunia×hybrida* selection identified as X01.85.1, not patented, as the female, or seed parent, with a proprietary *Petunia×hybrida* selection identified as X01.131.1, not patented, as the male, or pollen parent. The new *Petunia* was selected as a single plant from the resulting progeny of the cross-pollination by the Inventor in a controlled environment in Cobbitty, New South Wales, Australia in October, 2002.

Asexual reproduction of the new cultivar by vegetative cuttings in Cobbitty, New South Wales, Australia since October, 2002, has shown that the unique features of this new *Petunia* are stable and reproduced true to type in successive generations.

SUMMARY OF THE INVENTION

Plants of the cultivar MP209 have not been observed under all possible environmental conditions. The phenotype may vary somewhat with variations in environment such as temperature and light intensity without, however, any variance in genotype.

The following traits have been repeatedly observed and are determined to be the unique characteristics of 'MP209'. These characteristics in combination distinguish 'MP209' as a new and distinct cultivar:

1. Compact, low mounding and outwardly spreading plant habit.
2. Freely branching and vigorous growth habit.
3. Numerous small bright pink to light red purple-colored flowers.
4. Good garden performance.

Plants of the new *Petunia* differ primarily from plants of the parent selections in petal coloration as plants of the female parent selection have pink-colored petals and plants of the male parent selection have red-colored flowers.

Plants of the new *Petunia* can be compared to plants of the cultivar Red MP101, disclosed in U.S. Plant Pat. No. 14,998. In side-by-side comparisons conducted in Cobbitty, New South Wales, Australia, plants of the new *Petunia* differed primarily from plants of the cultivar Red MP101 in petal coloration as plants of the cultivar Red MP101 had red-colored petals.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

The photograph at the bottom of the sheet comprises a side perspective view of a typical flowering plant of 'MP209' grown in a container.

The photograph at the top of the sheet comprises a close-up view of typical leaves and flowers of 'MP209'.

DETAILED BOTANICAL DESCRIPTION

The aforementioned photographs and following observations and measurements describe plants grown in Lompoc, Calif., under commercial practice during the winter and early spring in a polycarbonate-covered greenhouse with day temperatures ranging from 21° C. to 24° C., night temperatures ranging from 16° C. to 18° C., and light levels ranging from 5,000 to 9,000 foot candles. Plants were grown for about 14 weeks with one plant per 14-cm container. Plants were pinched once about three weeks after planting. In the following description, color references are made to The Royal Horticultural Society Colour Chart, 1995 Edition, except where general terms of ordinary dictionary significance are used.

Botanical classification: *Petunia×hybrida* cultivar MP209.

Parentage:

*Female parent.*—Proprietary *Petunia* selection identified as X01.85.1, not patented.

*Male parent.*—Proprietary *Petunia* selection identified as X01.131.1, not patented.

Propagation:

*Type cutting.*—Vegetative cuttings.

*Time to initiate roots.*—About two weeks at 22° C.

*Time to produce a rooted young plant.*—About three to four weeks at 22° C.

*Root description.*—Fine, fibrous; white in color.

*Rooting habit.*—Freely branching, dense.

Plant description:

*Form.*—Annual flowering plant; indeterminate; initially upright, than low mounding and outwardly spreading; compact. Vigorous growth habit. Freely basal branching habit with about four main lateral branches per plant with lateral branches potentially forming at every node.

*Usage.*—Appropriate for hanging baskets, window boxes, patio containers and landscape applications.

*Plant height.*—About 11 cm.

*Plant diameter.*—About 40 cm.

*Lateral branches.*—Length: About 27 cm. Diameter: About 2.5 mm. Internode length: About 1.8 cm. Texture: Pubescent. Color: 144A.

*Foliage description.*—Arrangement, before flowering: Alternate, simple. Arrangement, when flowering: Opposite, simple. Length: About 2.8 cm. Width: About 1 cm. Shape: Elliptical. Apex: Acute. Base: Attenuate. Margin: Entire. Texture, upper and lower surfaces: Slightly glandular, viscid; pubescent. Venation pattern: Pinnate, arcuate. Color: Developing foliage, upper surface: 146A. Developing foliage, lower surface: 146B. Fully expanded foliage, upper surface: 146B. Fully expanded foliage, lower surface: 146C. Venation, upper surface: 144B. Venation, lower surface: 146D. Petiole length: About 4 mm. Petiole diameter: About 2 mm. Petiole texture, upper and lower surfaces: Smooth, glabrous. Petiole color, upper and lower surfaces: 144B.

Flower description:

*Flower type and habit.*—Small salverform flowers; flowers face upward or outward; single, axillary. Freely flowering, typically about eight to ten open flowers per lateral stem.

*Natural flowering season.*—Long day responsive; spring until frost in the autumn; flowering continuous during the flowering period.

*Flower longevity on the plant.*—About four to five days; flowers persistent.

*Fragrance.*—Faint; sweet.

*Flower size.*—Diameter: About 3 cm. Tube length: About 2.2 cm. Throat diameter, distal end: About 1 cm. Tube diameter, proximal end: About 2 mm.

*Flower buds.*—Length: About 2.5 cm. Diameter: About 5 mm. Shape: Elongated oblong with ruffled apices. Color: 69B.

*Corolla.*—Arrangement/appearance: Single whorl of five petals, fused into flared trumpet with distinct clefts between petal lobes. Petal lobe length: About 1.5 cm. Petal lobe width: About 1.5 cm. Petal shape: Roughly fan-shaped. Petal apex: Slightly acute. Petal margin: Entire. Petal texture, upper and lower surfaces: Smooth, satiny. Color: Petal, when opening, upper surface: 67B. Petal, when opening, lower surface: 62D. Petal, fully opened, upper surface: 67B to 67C; color becoming closer to 68A with development. Petal, fully opened, lower surface: 69B. Flower throat (inside): 157C. Flower tube (outside): 145B to 145C. Venation, upper petal surface: 67B. Venation, lower petal surface: 145D. Venation, throat: 154D. Venation, tube: 152D.

*Sepals.*—Arrangement/appearance: Single whorl of five sepals fused at base, star-shaped; slightly recurved. Length: About 9 mm. Width: About 2.5 mm. Shape: Linear. Apex: Rounded. Margin: Entire. Texture, upper and lower surfaces: Pubescent. Color, upper and lower surfaces: 144A.

*Peduncles.*—Length: About 1.5 cm. Width: About 1.25 mm. Angle: About 60° to the stem. Strength: Strong. Texture: Pubescent. Color: 144A.

*Reproductive organs.*—Stamens: Quantity/arrangement: Five per flower; stamens adnate to corolla tube. Anther shape: Ovoid. Anther length: About 1 mm. Anther color: 158A. Pollen amount: Scarce. Pollen color: 155A. Pistils: Quantity: One per flower. Pistil length: About 1.5 cm. Stigma shape: Rounded. Stigma color: 144A. Style length: About 1.2 cm. Style color: 145D. Ovary color: 145A.

*Fruit/seed.*—Fruit and seed production has not been observed.

Disease/pest resistance: Plants of the new *Petunia* have not been noted to be resistant to pathogens and pests common to *Petunia*.

Garden performance: Plants of the new *Petunia* have been observed to have good garden performance and to be tolerant to rain, wind and temperatures ranging from −5 to 40° C.

It is claimed:

1. A new and distinct cultivar of *Petunia* plant named 'MP209', as illustrated and described.

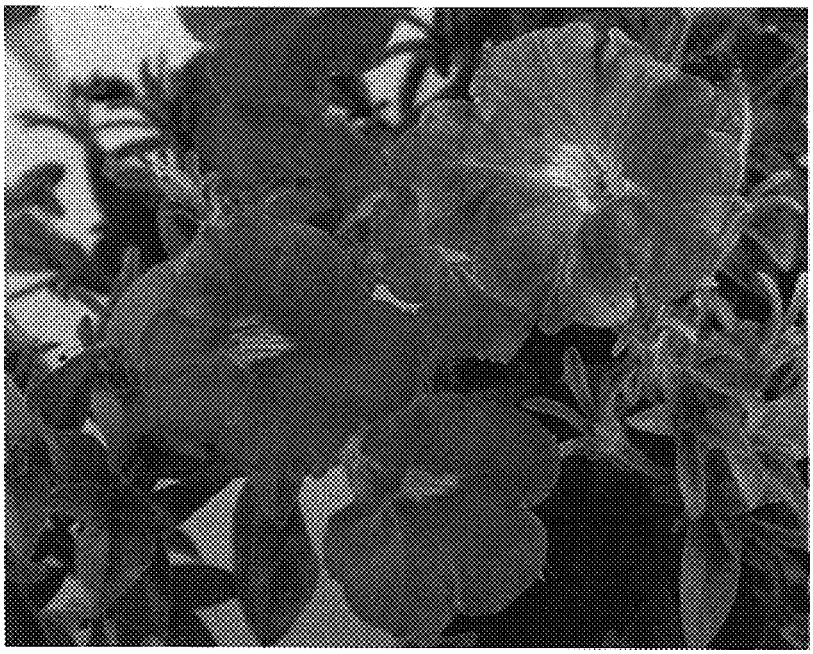
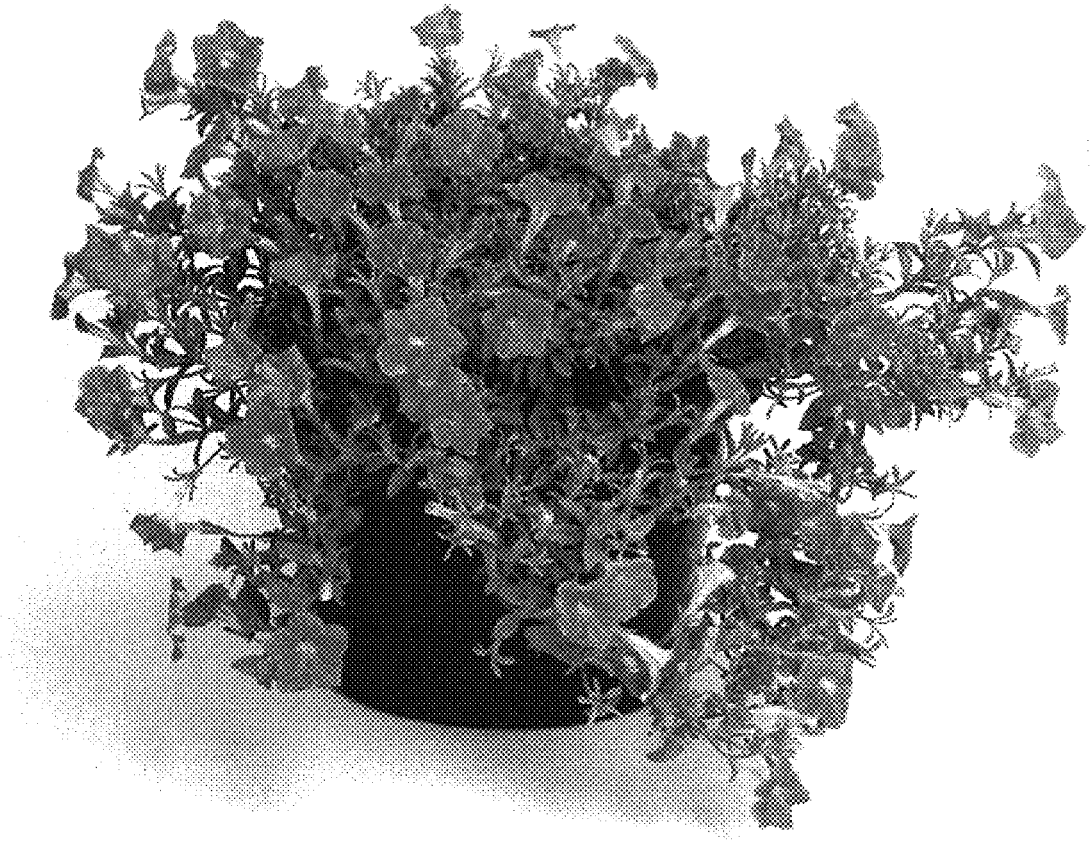

* * * * *